United States Patent [19]

Searcy

[11] Patent Number: 5,094,234
[45] Date of Patent: Mar. 10, 1992

[54] SOFT GOODS APPLIANCE FOR ELIMINATING CROTCH ITCH

[76] Inventor: Edwin B. Searcy, 1906 Centenary Dr., Richardson, Tex. 75081

[21] Appl. No.: 538,278
[22] Filed: Jun. 13, 1990
[51] Int. Cl.⁵ ............................................. A61F 5/40
[52] U.S. Cl. ........................................ 602/68; 602/73
[58] Field of Search ................... 128/95.1, 96.1, 100.1, 128/101.1, 891, 158, 159, 161, 891; 604/386, 387, 392

[56] References Cited

U.S. PATENT DOCUMENTS

| | | |
|---|---|---|
| 265,672 | 10/1882 | Hart . |
| 321,072 | 6/1885 | Winchester ........................ 128/161 |
| 792,424 | 6/1905 | King . |
| 850,298 | 4/1907 | DeMars . |
| 1,017,897 | 2/1912 | Montgomery ..................... 128/161 |
| 1,477,187 | 1/1922 | Rayne ............................ 128/161 X |
| 1,493,028 | 5/1924 | Fritsch ................................ 128/161 |
| 1,989,687 | 2/1935 | Deutsch ............................. 128/161 |
| 2,713,340 | 7/1955 | Meminger ........................... 128/161 |
| 3,294,086 | 12/1966 | Nelkin .................................. 128/78 |
| 3,504,671 | 4/1970 | Nelkin ................................ 128/158 |
| 3,664,336 | 5/1972 | Gelston .............................. 128/158 |
| 3,963,022 | 6/1976 | Rotello ............................... 128/158 |
| 4,014,044 | 3/1977 | Figueroa et al. ........................ 2/2 |
| 4,141,357 | 2/1979 | Dietz .................................. 128/159 |
| 4,155,360 | 5/1979 | Erickson ............................. 128/891 |
| 4,378,010 | 3/1983 | McDonald .......................... 128/168 |
| 4,526,167 | 7/1985 | Benal ................................. 128/158 |
| 4,622,962 | 11/1986 | Kauffman ........................... 128/158 |
| 4,759,355 | 7/1988 | Thrower ............................. 128/159 |

FOREIGN PATENT DOCUMENTS 858414  5/1940  France ....................................... 19/2

Primary Examiner—Mickey Yu
Assistant Examiner—Kerry Owens

[57] ABSTRACT

A soft goods appliance formed as a unit to be worn about the torso of a male user for eliminating crotch itch. Comprising the appliance is an elastic waistband from which a center strap extends downward from the rear and then toward the front between the user's buttocks in crotch contact. The front distal end of the center strap forms a concave pouch in which to receive the scrotum intervening between the scrotum and penis while maintaining separation between the scrotum and thighs. Vertically oriented side straps on the front of the appliance secure the pouch to spaced apart front portions of the waistband and cooperate with the center strap to define leg openings by which the unit can be drawn up in a wearing relation.

7 Claims, 2 Drawing Sheets

SOFT GOODS APPLIANCE FOR ELIMINATING CROTCH ITCH

FIELD OF THE INVENTION

The invention is related to the art of a soft goods body appliance to be worn by a male user for reducing or eliminating the discomfort of a dermatitis condition known as "jock itch".

BACKGROUND OF THE INVENTION

What is commonly referred to as "jock itch" is actually a dermatitis condition that occurs in the crotch between the buttocks and between the scrotum and upper thigh/groin areas of male persons. The condition tends to produce a general discomfort and extreme itch extending from behind the scrotum and upward toward the anus. Perspiration and nervousness tend to increase its severity as do tight pants and/or briefs which further restrict air circulation in the area. The condition strikes men of all ages and represents a state of misery to all those who encounter it.

Scientifically, those in the medical profession refer to jock itch as either intertrigo from rubbing or chafing or teniacruria caused by a bacteria fungus.

DESCRIPTION OF THE PRIOR ART

Frequent bathing up to several times per day is known to afford some relief from the more chronic instances of jock itch but is temporary at best. Other approaches toward relief most frequently resorted to involve applying medicaments to the affected areas in the form of ointments, creams, powder, sprays, etc. Despite vast amounts of money having been spent in the development and purchase of such medicaments, their effectiveness has been proven to be limited and fall considerably short of the more permanent relief sought by the user.

OBJECTS OF THE INVENTION

It is an object of the invention is to provide a novel article for effectively eliminating jock itch.

It is a further object of the invention to provide the article of the previous object in the form of a soft goods appliance to be worn by a male user for whom jock itch elimination is sought.

It is a still further object of the invention to provide the appliance of the previous objects as either a reusable or throwaway item and one which can be optionally be utilized as an attachment to undershorts or briefs commonly worn by men.

SUMMARY OF THE INVENTION

The invention relates to a male soft good appliance that when worn against the body, effectively eliminates the misery and discomfort normally associated with jock itch. More specifically, the invention relates to such an appliance comprised of an elastic waistband having a center strap and/or fabric extending downward and forward past the anus to within the crotch between the buttocks to a cup-like pouch formation in which to receive the scrotum. Side straps on the front side secure the scrotum pouch to the front of the waistband in a manner separating the penis from the scrotum while enabling the penis to remain uncovered for urination when required.

By virtue of the center strap being of a soft padded or unpadded fabric in crotch contact it essentially separates and isolates the buttocks from each other while the pouch separates the scrotum from the thighs. It has been found that for so long as the appliance is worn, it provides substantially permanent relief from the misery and discomfort of jock itch. At the same time, the center strap serves as a practical restraint against chafing between the buttocks and to rectal spotting when present. Moreover, the appliance can be worn comfortably and unnoticeably or can be buttoned or otherwise attached to undershorts or briefs when preferred.

The above-noted features and advantages of the invention as well as other superior aspects thereof will be further appreciated by those skilled in the art upon reading the detailed description which follows in conjunction with the drawings.

DESCRIPTION OF THE PREFERRED EMBODIMENT

Figure 1:
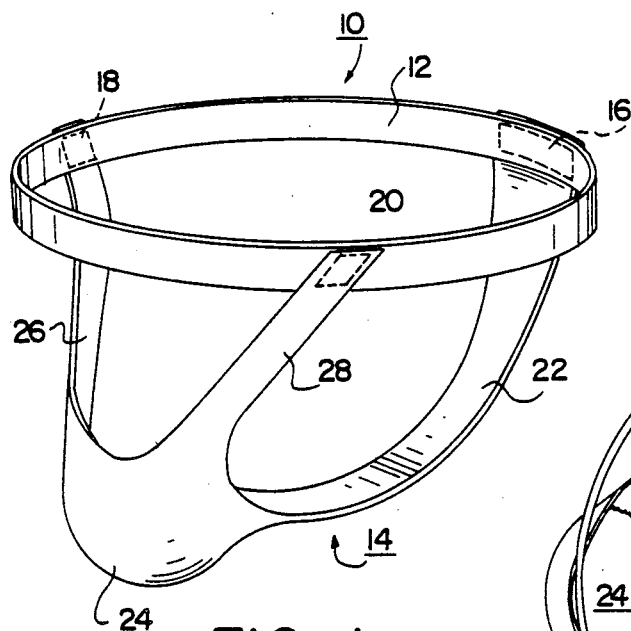
FIG. 1 is an isometric view of a first embodiment of the male appliance in accordance with the invention.
Figure 2:
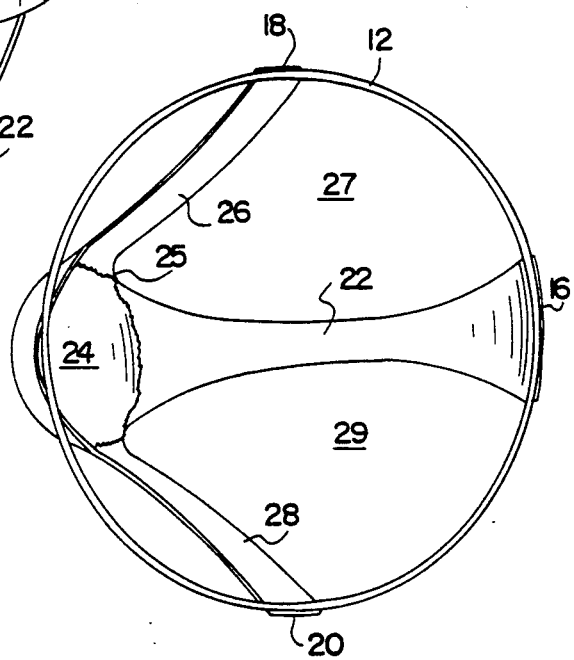
FIG. 2 is a top view of the appliance of FIG. 1.
Figure 3:
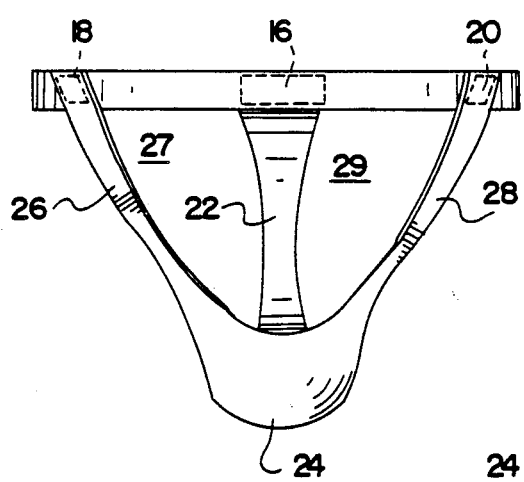
FIG. 3 is a front view of the appliance of FIG. 1.
Figure 4:
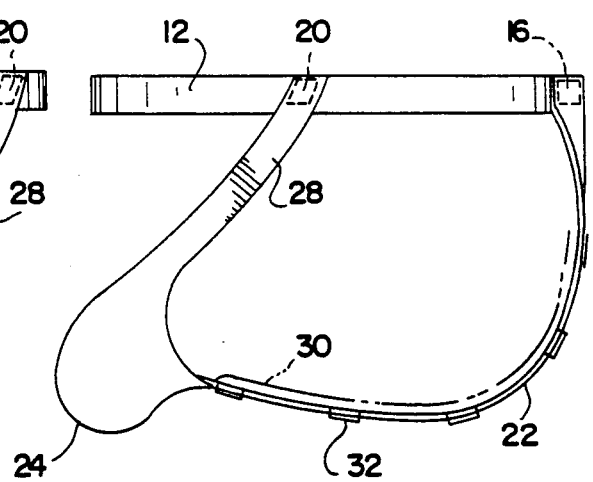
FIG. 4 is a side view of the appliance of FIG. 1.

In the description which follows, like parts are marked throughout the specification and drawings with the same reference numerals respectively. The drawing figures are not necessarily to scale and the proportions of certain parts may have been exaggerated for purposes of clarity.

Figure 7:
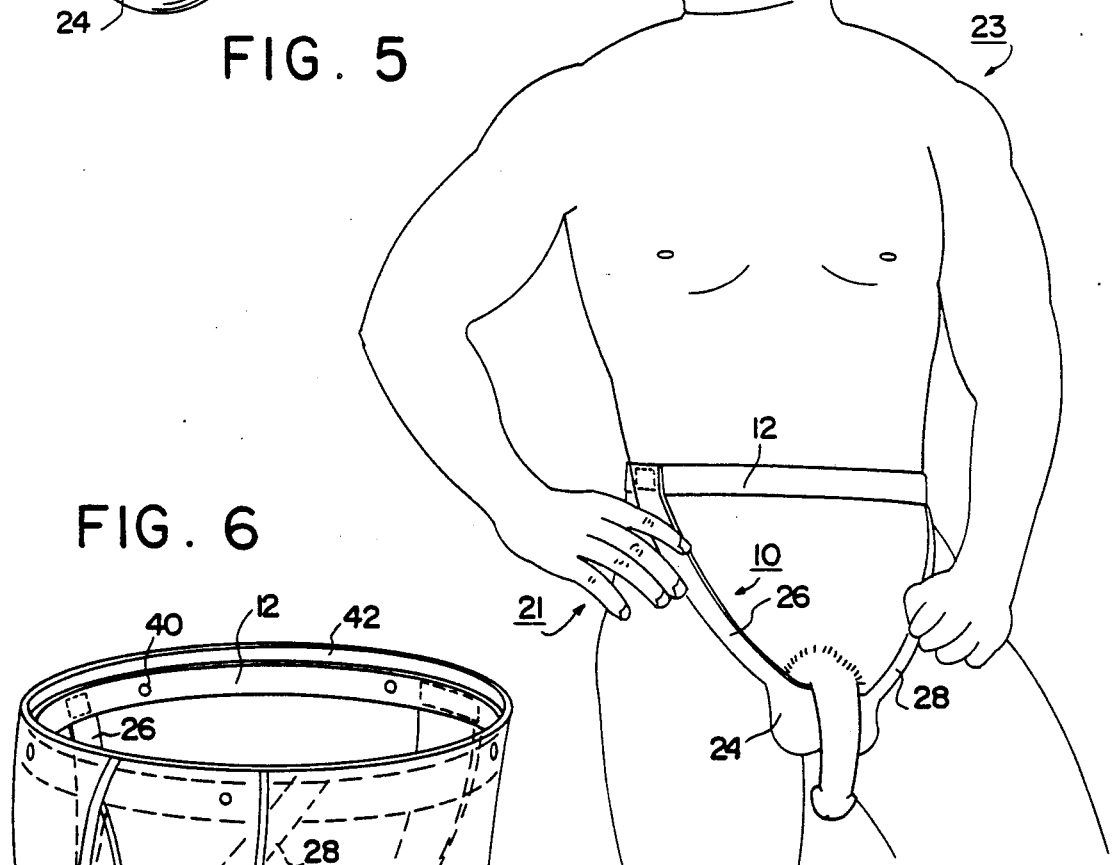
FIG. 7 is a fragmatic view illustrating the appliance hereof as worn by a male user.
Figure 5:
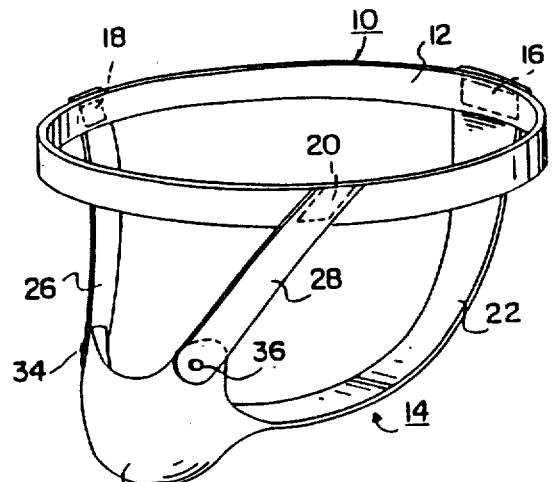
Figure 7:
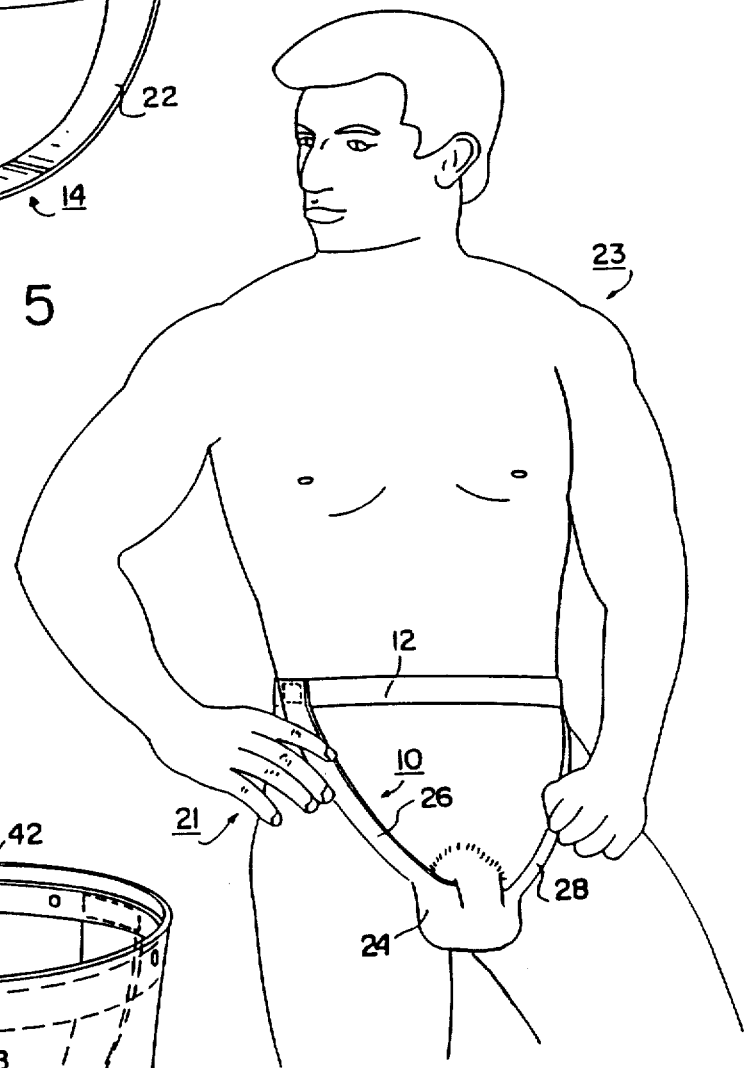
Figure 6:
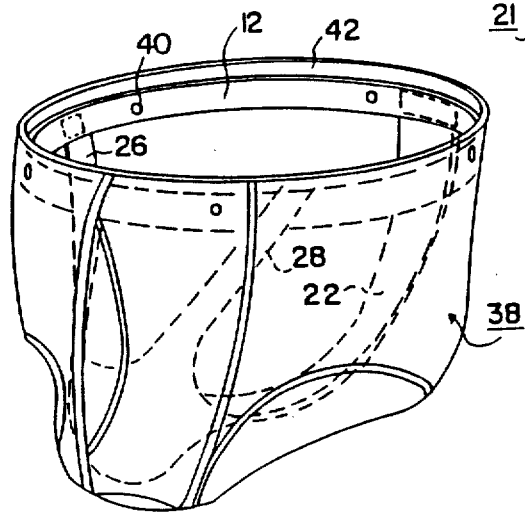

Referring to FIGS. 1-4, the appliance hereof is designated 10 and in the first embodiment is comprised of an elastic waistband 12 to which the under portion 14 is secured as by stitching at rear location 16 and side locations 18 and 20. It is intended that the appliance will be worn in skin contact beneath undershorts or brief of a male user such as illustrated in FIG. 7 on the torso 21 of a man 23. Comprising the under portion 14 is a center strap 22 of a suitable moisture absorbent fabric composition such as cotton. The strap extends downward from location 16 to extend in the crotch of the wearer to a concave scrotum pouch 24 gathered by elastic at 25. The pouch is held by side straps 26 and 28 and is secured to waistband 12 at side locations 18 and 20. Between the straps are defined leg openings 27 and 29.

It is preferred that the appliance embodiment illustrated in these figures be of a washable composition so as to render the appliance reusable for a reasonable life expectancy of several months. Alternatively, the composition of the appliance need not have washable characteristics but rather can be comprised of relatively inexpensive throw away type materials. Optionally, as illustrated in phantom in FIG. 4, an elongated pad 30 may be positioned in the critical area that snaps into place via undersnaps 32 onto center strap 22. As a further alternative, pad 30 could be secured in position via a velcro matching (not shown) between the pad and the center strap 22. Use of the pad would normally be limited to situations where excessive perspiration or other fluids would likely be encountered in the crotch area.

Figure 5:
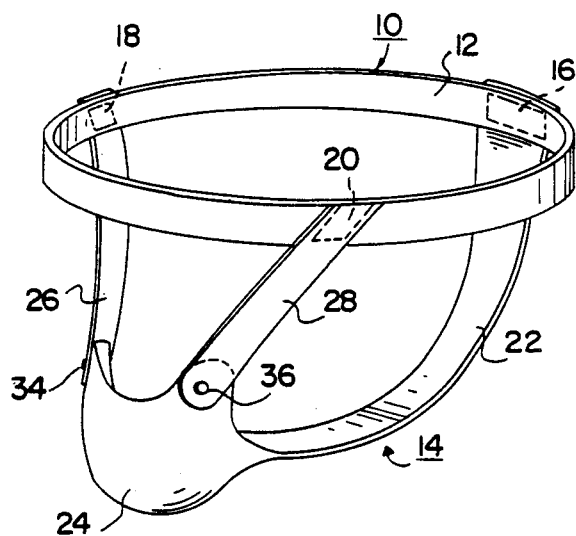
FIG. 5 is an isometric view of a modified appliance of FIG. 1.

For the embodiment of FIG. 5, the appliance 10 hereof includes snap connectors 34 and 36 that join side straps 26 and 28 respectively in a hinge relation to the scrotum pouch 24. Some users may find this embodiment somewhat easier to install beneath the undershorts and can even be secured together with the undershorts already in place. At the same time, the snap connectors 34 and 36 afford some versatility in adjusting the appliance into a more comfortable fit on the user.

Figure 6:
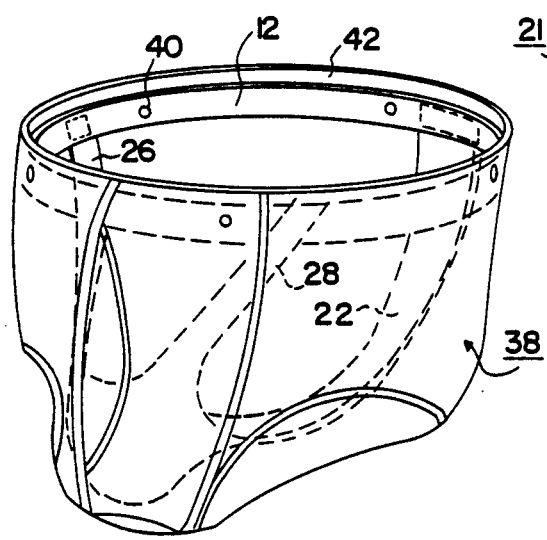
FIG. 6 is a further isometric view of the appliance of FIG. 1 as adapted for attached use in underbriefs.

For the embodiment of FIG. 6, the appliance 10 is secured internally of a man's underbrief 38 by means of snap connectors 40 on the appliance. The connectors are located externally about waistband 12 for cooperating with the snap receiver (not shown) located internally about the waistband 42 of the brief 38. In this arrangement, the brief and appliance can be marketed and worn by the user as a unit but can be conveniently separated for washing when desired.

By the above description, there is enclosed a novel softwear appliance that is highly effective in eliminating the miseries and discomfort normally associated with jock itch. The appliance is relatively simple and inexpensive to fabricate enabling it to be readily affordable by sufferers of the malady. While simple in concept, the appliance is highly effective to eliminate the discomforts of jock itch by simply eliminating the environment in which the bacteria grows and from which the jock itch is caused. Various options in construction are provided whereby the appliance can be modified to suit different markets and/or specific needs which some users may prefer. While simple in concept, the appliance is indeed effective in affording jock itch relief so as to fulfill a long-felt need in this area of discomfort.

Since many changes could be made in the above construction and many apparently widely different embodiments of this invention could be made without departing from the scope thereof, it is intended that all matter contained in the drawings and specification will be interpreted as illustrative and not in a limiting sense.

I claim:

1. A soft goods appliance for eliminating male crotch itch comprising:

a waistband adapted to surround the torso of a wearer in body contact therewith;

strap means attached to said waist band so as to define individual leg openings by which the strap means and waistband can be drawn upward onto the torso of a user;

said strap means being of a moisture absorbing composition and including a center strap extending from the rear of said waistband toward the front to fold between the buttocks and in crotch contact with the user; and a pouch means defined at the frontal end of and attached to said strap for receiving the scrotum in a relation intervening between the scrotum and the penis thereat; and a first attachment means integral with said waistband for securing the unit within a male undergarment having compatible second attachment means releasably cooperating with said first attachment means.

2. A soft goods appliance unit in accordance with claim 1 in which the appliance unit is comprised of a disposable throwaway composition.

3. A soft goods appliance unit in accordance with claim 1 in which said waistband, said strap means and said pouch are comprised of reusable washable compositions.

4. A soft goods appliance unit in accordance with claim 3 in which the waistband is of an elastic composition and said strap means and pouch are of a washable fabric.

5. A soft goods appliance unit in accordance with claim 1 in which said strap means includes a pair of upstanding spaced apart side straps securing said pouch to the front of said waistband.

6. A soft goods appliance unit in accordance with claim 5 in which said side straps are secured to said pouch with a hinge connection.

7. A soft goods appliance unit in accordance with claim 1 in which said center strap includes fastener means on the underside for securing an elongated moisture absorbent pad along the top side.

* * * * *

UNITED STATES PATENT AND TRADEMARK OFFICE
CERTIFICATE OF CORRECTION

PATENT NO. : 5,094,234  Page 1 of 2
DATED : March 10, 1992
INVENTOR(S) : Edwin B. Searcy It is certified that error appears in the above-indentified patent and that said Letters Patent is hereby corrected as shown below:

IN THE DRAWINGS:

Sheet 2 of 2 should be deleted to appear as per attached sheet of drawings.

Signed and Sealed this

Second Day of November, 1993

Attest:

BRUCE LEHMAN

Attesting Officer   Commissioner of Patents and Trademarks